United States Patent [19]

Papenfuhs et al.

[11] 4,110,375
[45] Aug. 29, 1978

[54] NOVEL 2-HYDROXYNAPHTHALENE-1-ALDEHYDES, PROCESS FOR PREPARING THEM AND THEIR USE

[75] Inventors: Theodor Papenfuhs, Frankfurt am Main; Heinrich Volk, Bad Vilbel, both of Fed. Rep. of Germany

[73] Assignee: Hoechst Aktiengesellschaft, Frankfurt am Main, Fed. Rep. of Germany

[21] Appl. No.: 835,299

[22] Filed: Sep. 21, 1977

Related U.S. Application Data

[62] Division of Ser. No. 707,751, Jul. 22, 1976, Pat. No. 4,064,349.

[30] Foreign Application Priority Data

Jul. 30, 1975 [DE] Fed. Rep. of Germany ....... 2533960

[51] Int. Cl.² ............................................. C07C 103/22
[52] U.S. Cl. .............................. 260/559 R; 260/562 R
[58] Field of Search ......................... 260/559 R, 562 R

[56] References Cited

U.S. PATENT DOCUMENTS 3,892,803  7/1975  Diamond et al. ................ 260/559 R

FOREIGN PATENT DOCUMENTS 952,629  11/1956  Fed. Rep. of Germany ...... 260/559 R
794,885   5/1958  United Kingdom ................ 260/559 R

*Primary Examiner*—Winston A. Douglas
*Assistant Examiner*—J. V. Howard
*Attorney, Agent, or Firm*—Connolly and Hutz

[57] ABSTRACT

Novel 2-hydroxynaphthalene-1-aldehydes have been found which have the general formula (I)

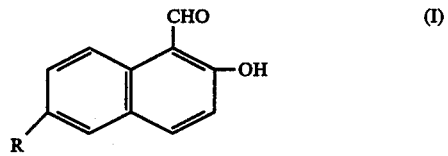

wherein R is a carboxylic acid group, a carboxylic acid ester group, preferably of an alkanol or of an optionally substituted phenol, an optionally substituted carboxylic acid amide group, or an optionally substituted carboxylic acid hydrazide group, which are very valuable intermediate products for the preparation of coloring agents, optical brighteners, textile auxiliary agents and pharmaceutical products.

3 Claims, No Drawings

NOVEL 2-HYDROXYNAPHTHALENE-1-ALDEHYDES, PROCESS FOR PREPARING THEM AND THEIR USE

This application is a division of application Ser. No. 707,751 filed July 22, 1976, now U.S. Pat. No. 4,064,349.

The present invention relates to novel 2-hydroxynaphthalene-1-aldehydes, to a process for preparing them and their use.

Novel 2-hydroxynaphthalene-1-aldehydes have been found which have the general formula (I)

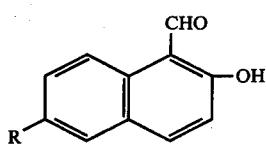   (I), wherein R is a carboxylic acid group, a carboxylic acid ester group, preferably of an alkanol or of an optionally substituted phenol, an optionally substituted carboxylic acid amide group, or an optionally subtituted carboxylic acid hydrazide group.

Carboxylic acid alkyl ester groups are preferably those having from 1 to 5 carbon atoms in the alkyl radical which may be straight-chained or branched or substituted, for example by phenyl or by a phenyl radical subtituted by one or more, preferably 1, 2 or 3 substituents selected from the group of chlorine, fluorine, bromine, methyl, ethyl, methoxy, ethoxy, trifluoromethyl, nitro, acetylamino, cyano and carboxylic acid phenyl ester, in which the phenyl radical may be substituted by one or more, preferably 1, 2 or 3 substituents selected from chlorine, bromine, fluorine, methyl, ethyl, methoxy, ethoxy, trifluoromethyl, nitro, acetylamino and cyano.

Substituted carboxylic acid amide radicals are in particular those which contain at the N-atom 1 or 2 alkyl radicals, especially those having from 1 to 4 carbon atoms, which may be further subtituted, or contain one aryl radical, such as for example a phenyl radical or a naphthyl radical which may be substituted, or those which contain one of the above-mentioned alkyl radicals and one aryl radical each bound at the nitrogen atom. Of these, there are to be mentioned in particular carboxylic acid amide groups which have the formula

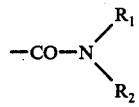

in which $R_1$ stands for hydrogen, an alkyl group having from 1 to 4 carbon atoms which may be substituted by lower alkoxy, such as methoxy and/or ethoxy, or by hydroxy or halogen, especially chlorine or bromine, $R_2$ has the meaning of R or represents a phenyl radical optionally substituted by one or more, preferably 1, 2 or 3 substituents selected from the group consisting of fluorine, chlorine, bromine, methyl, ethyl, methoxy, ethoxy, trifluoromethyl, nitro or cyano, or is the benzyl or phenethyl radical.

Substituted carboxylic acid hydrazides are particularly those which contain an aryl radical at the nitrogen atom in the β-position and/or an alkyl radical at the nitrogen atom in the α- and/or β-position. Of these, there are to be mentioned, besides the carboxylic acid hydrazide group itself, those carboxylic acid hydrazide radicals which have the formula

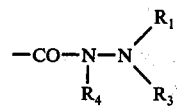

in which $R_1$ is defined as above, $R_4$ is different from $R_1$ or is identical with it and has the meaning of $R_1$, and $R_3$ stands for an alkyl radical having from 1 to 4 carbon atoms, or for the benzyl or phenethyl radical or for a naphthyl or phenyl radical, each of which may be substituted in the benzene nucleus by one or several, preferably 1, 2 or 3 substituents selected from the group consisting of fluorine, chlorine, bromine, methyl, ethyl, methoxy, ethoxy, trifluoromethyl, nitro, acetylamino and cyano, in which case at least one of the three substituents $R_1$, $R_3$ and $R_4$ is no hydrogen atom.

The novel 2-hydroxynaphthalene-1-aldehydes can be prepared according to the invention by a process which comprises reacting a 2-hydroxynaphthalene of the formula (II)

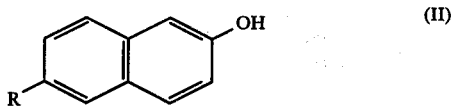

in which R is defined as above, with hexamethylene-tetramine, in the presence of an optionally halogenated, for example chlorinated, lower aliphatic mono- or dicarboxylic acid.

The 2-hydroxynaphthalenes of the formula (II) used as starting compounds may be obtained by carboxylation of 2-hydroxynaphthalene-potassium (cf. German Pat. No. 436,524) and, optionally, by a subsequent conversion of the 2-hydroxynaphthalene-6-carboxylic acid thus obtained into the esters, amides or hydrazides thereof.

The process is preferably carried out in such a manner that the starting compound of the formula (II) and hexamethylene-tetramine are dissolved or suspended in generally two to ten times the amount of aliphatic carboxylic acid and are heated for a longer period of time at a temperature of up to 120° C, preferably in the range of from 80° to 100° C, in which process the addition of a small amount of mineral acid, such as sulfuric acid or hydrochloric acid, is required, except for a reaction wherein trifluoroacetic acid is used as a halogenated aliphatic acid. The acid may be added directly in admixture with the carboxylic acid, or may be added subsequently.

As lower carboxylic acids there are suitable for the reaction in particular acetic acid, but also propionic acid, butyric acid or valeric acid, moreover, dicarboxylic acids, such as adipic acid or malonic acid, or halogenated fatty acids, such as chloroacetic acid, trichloroacetic acid or trifluoro-acetic acid.

Hexamethylene-tetramine may also be replaced by a mixture of ammonia and formaldehyde having an analogous effect, in which process ammonia and formaldehyde may be used in an aqueous solution or in the gaseous state.

The hexamethylene-tetramine is used in a stoichiometrical amount or in a small excess amount. In addition to that, also paraformaldehyde in a molar ratio of from 1:1 to 3:1, calculated on the starting compound of the formula (II), can be used.

The 2-hydroxynaphthalene-1-aldehydes of the invention are valuable intermediate products for the preparation of dyestuffs, optical brighteners, textile auxiliary agents and pharmaceutical compounds. They are particularly suitable for the preparation of azomethine dyes which are obtained by the condensation of these aldehydes with suitable amines.

Thus, they yield for example, by the condensation of 1 mole of the aldehyde with 1 mole of an isocyclic or heterocyclic monoamine, compounds of the formula

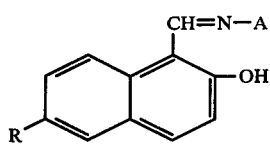

wherein R is defined as above and A represents an isocyclic or heterocyclic radical, which are suitable as coloring agents; by the condensation of 2 moles of aldehyde (I) with 1 mole of hydrazine or of an aliphatic, isocyclic or heterocyclic diamine, compounds were also obtained in an analogous manner which are suitable as dyeing agents having very good properties and which correspond to the formula

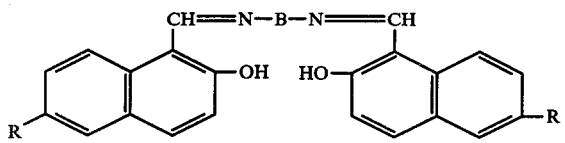

in which R is defined as above and R represents a single bond, a straight-chain or branched alkylene radical possibly interrupted by hetero atoms, a bivalent group and/or an isocyclic ring, or represents a cycloalkylene radical, an arylene or a heterocyclic radical, or corresponding metal complex compounds are obtained by subsequent metallization.

The mono- and diazomethine compounds which can thus be obtained from the novel naphthaldehyde (I), are suitable for the pigmentation of printing pastes, of high-molecular-weight plastic compositions or lacquers, and in this respect they show better fastness properties with regard to solvents and more pure colour shades than the known isomeric dyestuffs prepared from those aldehydes which show the grouping R in the 3-position (cf. French Pat. Nos. 1,503,786 and 1,449,666).

Furthermore they yield lacquer coatings having a very good fastness to cross-lacquering, and possess a good fastness to bleeding in plasticized polyvinylchloride.

Those compounds of the formula (I), in which R represents the carboxy group, a carboxylic acid-alkylester radical having from 1 to 4 carbon atoms in the alkyl group, the carboxylic acid amide group, a carboxylic acid-mono-($C_1$-$C_4$-alkyl)-amide group, a carboxylic acid-di-($C_1$-$C_4$-alkyl)-amide group, the carboxylic acid-phenylamide or the carboxylic acid-phenylhydrazide group, as well as the naphthaldehyde compounds of the Examples 1, 3, 4, 5 and 6 are of particular interest.

The following Examples serve to illustrate the invention; the parts being parts by weight.

EXAMPLE 1

3 Parts of paraformaldehyde, 18.8 parts of 2-hydroxynaphthalene-6-carboxylic acid and 14 parts of hexamethylene-tetramine (urotropine) were introduced one after the other into 35 parts of glacial acetic acid at room temperature, while stirring thoroughly. The reaction mixture was subsequently heated for 3 hours at 80° C. After 75 parts of glacial acetic acid and a mixture of 9 parts of water and 15 parts of sulfuric acid of 95% strength had been added, the mixture was heated for another 5 hours at 80° C. Subsequently 75 parts of hot water were added, and the reaction mixture was cooled. The precipitate was filtered off with suction and was washed with warm water until neutral. After drying, 17 parts of the aldehyde of the formula

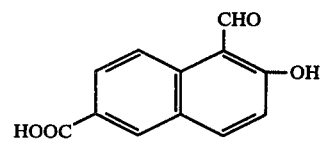

were obtained, which had a melting point of 309° C.

Analysis: $C_{12}H_8O_4$ Calc. C, 66.6%; H 3.7%. Found C, 66.8%; H 3.7%. Molar mass: 216 (mass spectrum).

Phenylhydrazone: melting point 288° C
Molar mass: 306 (mass spectrum).

EXAMPLE 2

18.8 parts of 2-hydroxynaphthalene-6-carboxylic acid, 20 parts of hexamethylene-tetramine and 5 parts of paraformaldehyde were introduced into 180 parts of glacial acetic acid, while stirring. Subsequently 40 parts of concentrated hydrochloric acid were slowly added dropwise, and the mixture was heated for 1 hour at a temperature in the range of from 90° to 100° C. After 40 parts of concentrated hydrochloric acid had again been added, the reaction mixture was heated once more for 1 hour at a temperature of from 90° to 100° C. Subsequently 150 parts of hot water were added, and the mixture was allowed to cool. The precipitate was filtered off and was washed with warm water until neutral. After drying, 15 parts of an aldehyde were obtained, which was identical with the one obtained according to Example 1.

EXAMPLE 3

If in Example 1 the 2-hydroxy-naphthalene-6-carboxylic acid was replaced by 18.7 parts of 2-hydroxy-naphthalene-carboxylic acid-amide, 16.3 parts of the aldehyde of the formula

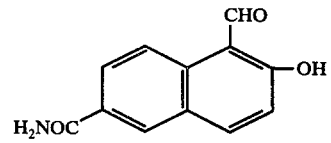

were obtained, which had a melting point of 285° C.

Analysis: $C_{12}H_9NO_3$ Calc. C, 67.0%; H 4.2%; N 6.5%. Found C, 66.7%; H 4.2%; N 6.3%. Molar mass: 215 (mass spectrum).

EXAMPLE 4

If in Example 1 the 2-hydroxy-naphthalene-6-carboxylic acid was replaced by 26.3 parts of 2-hydroxynaphthalene-6-carboxylic acid anilide, 25 parts of the aldehyde of the formula

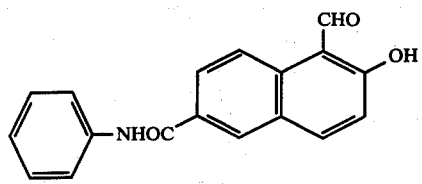

were obtained, which had a melting point of 308° C.

Analysis: $C_{18}H_{13}NO_3$ Calc. C, 74.2%; H, 4.5%; N, 4.8%. Found C, 74.5%; H, 4.3%; N, 5.0%. Molar mass: 291 (mass spectrum).

EXAMPLE 5

If in Example 1 the 2-hydroxy-naphthalene-6-carboxylic acid was replaced by 20.2 parts of 2-hydroxy-naphthalene-6-carboxylic acid-methylester, 17.4 parts of the aldehyde of the formula

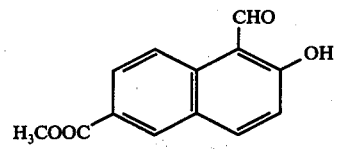

were obtained, which had a melting point of 205° C. Molar mass: 230 (mass spectrum). In an analogous manner, the following aldehydes of the formula I were obtained:

| Example | R | Molar mass (mass spectrum) | Melting point |
|---|---|---|---|
| 6 | —COOCH$_2$CH$_2$CH$_2$CH$_3$ | 272 | 83° C |
| 7 | —CONHCH$_3$ | | |
| 8 | —CONHCH$_2$CH$_2$CH$_2$CH$_3$ | | |
| 9 | —CON(C$_4$H$_9$)$_2$ | | |
| 10 | —CONH—⟨⟩—OCH$_3$ | | |
| 11 | —CONHNH—⟨⟩ | | |

EXAMPLE 12

14.9 Parts of 5-aminobenzimidazolone as well as 21.6 parts of 1-formyl-2-hydroxy-naphthalene-6-carboxylic acid were introduced, while stirring, at room temperature into a mixture of 130 parts of ethanol and 20 parts of glacial acetic acid. Subsequently the mixture was heated at boiling point for 3 hours. The residue was suction-filtered, while still hot, and was washed well with ethanol. The moist product was heated to 100° C in 80 parts of dimethylformamide, was again suction-filtered, while hot, and washed once more thoroughly with ethanol. After drying, 32.1 parts of a bright yellow dyestuff of the formula

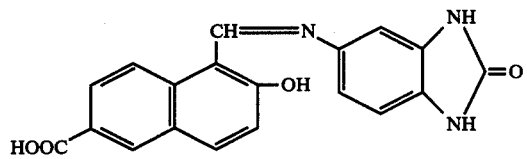

were obtained, which dyed polyvinyl chloride in clear yellow shades with excellent fastness properties.

EXAMPLE 13

If in Example 12 the 1-formyl-2-hydroxy-naphthalene-6-carboxylic acid was replaced by 21.5 parts of the aldehyde described in Example 3, 28 parts of a yellow azomethine pigment were obtained, which had the formula

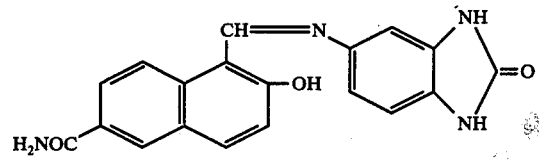

A lacquer which was pigmented with this compound yielded yellow lacquer coatings having a good fastness to light and to cross lacquering.

If in Example 12 the 5-amino-benzimidazolone was replaced by the amines indicated in Table 1 below, the corresponding azomethine compounds were obtained having very good pigment properties as to the fastness to light and over-varnishing.

Table 1

| Example | Amine | Color shade of the azomethine compound |
|---|---|---|
| 14 | H$_2$N—⟨⟩—NHCO—⟨⟩ | yellow |
| 15 | H$_2$N—⟨⟩—CONH—⟨⟩ | yellow |
| 16 | H$_2$N—⟨⟩(OCH$_3$)(Cl)—NHCO—⟨⟩ | orange |
| 17 | H$_2$N—⟨⟩—N=N—⟨⟩ | red |
| 18 | H$_2$N—⟨⟩(OCH$_3$)(O$_2$N)—NHSO$_2$—⟨⟩ | orange |

EXAMPLE 19

A mixture of 21.6 parts of 6-carboxy-2-hydroxy-1-naphthaldehyde, 36.6 parts of 6'-aminobenzimidazolonyl-azo-5'-acetoacetic acid-4-toluidide and 700 parts of water was ground at the pump-over device by means of a corundum disk attrition mill for 30 minutes under a nitrogen atmosphere. The suspension obtained was passed with the exclusion of oxygen into a flask, and the condensation was carried out within 6 hours, while stirring and increasing the reaction temperature steadily from 30° to 100° C. In order to avoid any secondary reactions, a slight inert gas current was passed through the suspension during this time. After an internal temperature of 100° C had been reached, the mixture was continued to be stirred for 30 minutes, then it was filtered off with suction while hot, and was washed with hot water and dried at 80° C in the circulating air cabinet.

56.3 Parts of an orange-colored pigment having the formula

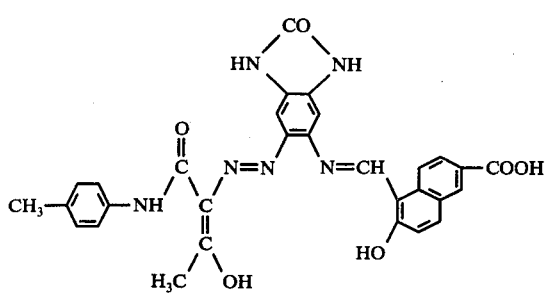

were obtained in a quantitative yield. The pigment could be used excellently for the preparation of dyeing of plastic materials and particularly of paints and lacquers, due to its high tinctorial strength and its good fastness to solvents and to light.

EXAMPLE 20

21.6 Parts of 1-formyl -2-hydroxy-6-naphthoic acid were added while stirring to 3.0 parts of 1,2-diaminoethane dissolved in 250 parts of ethanol and 10 parts of glacial acetic acid, and the mixture was heated for 3 hours at boiling point. After cooling, the yellow compound was suction-filtered and washed thoroughly with ethanol. The moist product was then introduced into 150 parts of dimethylformamide, was mixed with 9.0 parts of nickel diacetate and heated for 4 hours at 120° C. The yellow pigment thus obtained was filtered off with suction while hot and was washed thoroughly first with hot water and subsequently with ethanol. After drying, 30.2 parts of a yellow pigment were obtained, which had the formula

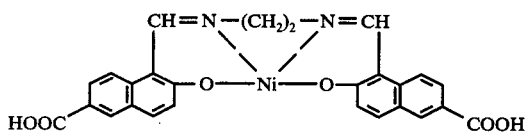

Ni: calculated 11.4%; found 11.3%,
and which dyed polyvinyl chloride in a clear yellow shade having excellent fastness properties.

EXAMPLE 21

21.6 Parts of 1-formyl-2-hydroxy-6-naphthoic acid, 3.0 parts of diaminoethane and 9.0 parts of nickel diacetate were heated in 300 parts of ethanol at boiling point for 5 hours. The yellow compound was filtered off with suction while hot and was washed thoroughly with hot water and ethanol. The product was then heated in 150 parts of dimethylformamide for 1 hour at 120° C, was filtered off while hot, and was washed thoroughly with hot water and ethanol. After drying, 31.0 parts of a yellow pigment were obtained, which was identical with the one obtained according to Example 20.

EXAMPLE 22

10.8 Parts of 1-formyl-2-hydroxy-6-naphthoic acid were introduced, while stirring, into 5.5 parts of 2-aminophenol in 100 parts of ethanol and 10 parts of glacial acetic acid, and the mixture was heated at the boiling point for 3 hours. After cooling, the yellow compound was filtered off, was washed thoroughly with ethanol and was then introduced once more into 100 parts of ethanol. Subsequently, 10.0 parts of copper acetate were added, and the whole was heated for 5 hours at boiling point. The compound formed was filtered off at 40° C and was washed with hot water and ethanol. After drying, 13.2 parts of a yellow-green pigment were obtained, which had the formula

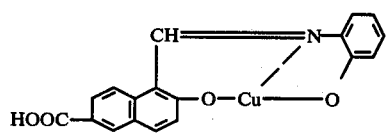

Cu: calculated 17.2%; found 17.0%,
and which permitted the preparation of lacquers having a metal effect and showing a good fastness to light and to cross-lacquering.

EXAMPLE 23

5.5 Parts of 2-aminophenol were added, while stirring, to 10.8 parts of 1-formyl-2-hydroxy-6-naphthoic acid and 10.0 parts of copper acetate in 100 parts of ethanol. Subsequently the mixture was heated for 6 hours at boiling point. The complex compound was filtered off at 40° C and was washed with hot water and alcohol. After drying, 12.5 parts of a yellow-green pigment were obtained, which was identical with the one prepared according to Example 22.

We claim:
1. A compound of the formula

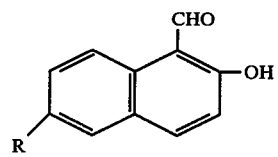

in which R is the group

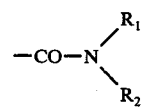

wherein $R_1$ is hydrogen or alkyl of 1 to 4 carbon atoms, and $R_2$ is hydrogen, alkyl of 1 to 4 carbon atoms or phenyl.
2. The compound of the formula of claim 1 in which R is carbonamide.
3. The compound of the formula of claim 1 in which R is carboxylic acid-phenylamide.

* * * * *